(12) United States Patent
Donaldson et al.

(10) Patent No.: US 7,740,584 B2
(45) Date of Patent: Jun. 22, 2010

(54) METHOD AND SYSTEM FOR MAPPING PHYSIOLOGY INFORMATION ONTO ULTRASOUND-BASED ANATOMIC STRUCTURE

(75) Inventors: Brenda Donaldson, Harrison Township, MI (US); Israel Raz, Highland Park, IL (US); Sachin Vadodaria, Fox Point, WI (US)

(73) Assignee: The General Electric Company, Schenectady, NY (US)

( * ) Notice: Subject to any disclaimer, the term of this patent is extended or adjusted under 35 U.S.C. 154(b) by 392 days.

(21) Appl. No.: 11/204,711

(22) Filed: Aug. 16, 2005

(65) Prior Publication Data

US 2007/0055150 A1 Mar. 8, 2007

(51) Int. Cl.
A61B 5/05 (2006.01)
A61B 8/14 (2006.01)

(52) U.S. Cl. .................. 600/443; 600/427; 600/466
(58) Field of Classification Search .................. 600/443, 600/466, 424; 601/2; 382/128; 606/27
See application file for complete search history.

(56) References Cited

U.S. PATENT DOCUMENTS

| | | | |
|---|---|---|---|
| 5,409,000 A | 4/1995 | Imran | |
| 5,409,007 A * | 4/1995 | Saunders et al. | 600/447 |
| 5,568,809 A * | 10/1996 | Ben-haim | 600/433 |
| 5,588,432 A | 12/1996 | Crowley | |
| 5,662,108 A | 9/1997 | Budd et al. | |
| 5,687,737 A | 11/1997 | Branham | |
| 5,713,946 A | 2/1998 | Ben-Haim | |
| 6,019,725 A | 2/2000 | Vesely et al. | |
| 6,086,532 A | 7/2000 | Panescu et al. | |
| 6,200,269 B1 | 3/2001 | Lin et al. | |
| 6,216,027 B1 | 4/2001 | Willis et al. | |
| 6,413,219 B1 | 7/2002 | Avila et al. | |
| 6,447,450 B1 | 9/2002 | Olstad | |
| 6,505,063 B2 * | 1/2003 | Van Den Brink et al. | 600/411 |
| 6,575,901 B2 | 6/2003 | Stoycos et al. | |
| 6,650,927 B1 | 11/2003 | Keidar | |
| 6,728,562 B1 | 4/2004 | Budd et al. | |

(Continued)

FOREIGN PATENT DOCUMENTS

WO 01/20552 A 3/2001

OTHER PUBLICATIONS http://medical.merriam-webster.com/medical/m-mode.*

(Continued)

*Primary Examiner*—Eric F Winakur
*Assistant Examiner*—Helene Bor
(74) *Attorney, Agent, or Firm*—Dean Small; The Small Patent Law Group

(57) ABSTRACT

A physiology system is provided that includes an ultrasound beamformer that is configured to receive signals from an ultrasound probe that is located proximate the region of interest. The system includes an ultrasound processor module for generating an ultrasound image, based on the ultrasound data, that is representative of an anatomical structure of a portion of the region of interest contained in the scan plane. A physiology signal processor module is also provided and configured to receive physiology signals from a catheter located proximate the region of interest. The physiology signal processor module produces physiology data representative of the physiology activity of the portion of the region of interest contained in the scan plane. A display processor module forms a display image combining the ultrasound image and physiology data.

32 Claims, 5 Drawing Sheets

U.S. PATENT DOCUMENTS

| | | |
|---|---|---|
| 2004/0097806 A1* | 5/2004 | Hunter et al. ............... 600/434 |
| 2004/0127798 A1 | 7/2004 | Dala-Krishna et al. |
| 2004/0152974 A1* | 8/2004 | Solomon .................... 600/424 |
| 2005/0013473 A1 | 4/2005 | Gordon et al. |
| 2005/0080336 A1* | 4/2005 | Byrd et al. .................. 600/428 |
| 2005/0096543 A1* | 5/2005 | Jackson et al. .............. 600/441 |
| 2006/0184016 A1* | 8/2006 | Glossop ...................... 600/434 |
| 2006/0229594 A1* | 10/2006 | Francischelli et al. ......... 606/27 |
| 2006/0253030 A1* | 11/2006 | Altmann et al. ............. 600/466 |
| 2006/0253031 A1* | 11/2006 | Altmann et al. ............. 600/466 |
| 2006/0253032 A1* | 11/2006 | Altmann et al. ............. 600/466 |

OTHER PUBLICATIONS

Radiology, vol. 121, 157-162, Copyright © 1976 by Radiological Society of North America.*

A. Milkowski, Y. Li, D. Becker, and S. O. Ishrak, "Speckle reduction imaging," Technical White Paper-General Electric Health Care (Ultrasound). Last accessed on Jul. 9, 2009. Available at http://www.gehealthcare.com/usen/ultrasound/education/docs/whitepaper_SRI.pdf.*

* cited by examiner

METHOD AND SYSTEM FOR MAPPING PHYSIOLOGY INFORMATION ONTO ULTRASOUND-BASED ANATOMIC STRUCTURE

BACKGROUND OF THE INVENTION

Embodiments of the present invention generally relate to methods and systems for combining physiology information with ultrasound based anatomic structures. More particularly, embodiments relate to methods and systems that construct a 2D or 3D representation of an anatomical structure based on ultrasound data and superimpose thereon graphical information representative of physiologic characteristics of the anatomic structure.

Various types of physiology workstations have been proposed such as electrophysiology (EP) workstations, hemodynamic (HD) workstations, and the like. Generally, EP, HD and ablation procedures are carried out through the use of, among other things, EP catheters, HD catheters and mapping sensors. The procedure room also includes a fluoroscopy system, a diagnostic ultrasound system, a patient monitoring device and an ablation system. The ultrasound system may utilize a variety of probes, such as ultrasound catheters, transesophageal probes, surface probes and the like. The ultrasound system may be used before, during or after an ablation procedure to monitor the position of the EP catheters and/or ablation catheters. The mapping system is utilized with physiology catheters (EP or HD) to detect and record desired physiologic parameters. The mapping system includes equipment to monitor and track the position of a mapping catheter, from which a map is created of the region of interest.

Conventional electrophysiology mapping systems utilize a mapping catheter positioned in a heart chamber that may include passive and active electrode sites. The active electrode sites impose an electric field within the chamber. The blood volume and wall motion modulate the electric field that is detected by passive electrode sites on the catheter. Electrophysiology measurements and geometric measurements are taken from the catheter and used to construct a map and to display intrinsic heart activity. Another type of conventional mapping system utilizes an external imaging modality such as ultrasound, SPECT, PET, MRI, CT system that is positioned external to the patient to capture a 3D image of the heart. The diagnostic image is captured before the heart is mapped. The mapping system utilizes data obtained from the catheter to generate a geometric map, with which the diagnostic image is then registered.

Heretofore, physiology workstations have operated independent and distinct from the mapping, ablation and ultrasound equipment utilized during the physiology study. Also, conventional mapping, ablation and ultrasound equipment have operated independent and distinct from one another. The mapping, ablation, physiology and ultrasound systems include separate computers, monitors, and user interfaces, all of which are mounted on separate chassis.

Conventional physiology, mapping, ablation and ultrasound systems suffer from various disadvantages that are addressed by various embodiments of the present invention.

BRIEF DESCRIPTION OF THE INVENTION

In accordance with at least one embodiment, a physiology system is provided that includes an ultrasound beam former that is configured to receive signals from an ultrasound probe that is located proximate the region of interest. The beam former, based on the receive signals, produces ultrasound data representative of a scan plane including the region of interest. The system also includes an ultrasound processor module for generating an ultrasound image, based on the ultrasound data, that is representative of an anatomical structure of a portion of the region of interest contained in the scan plane. The physiology signal processor module is also provided and configured to receive physiology signals from a catheter located proximate the region of interest. The physiology signal processor module produces physiology data representative of the physiologic activity of the portion of the region of interest contained in the scan plane. A display processor module forms a display image combining the ultrasound image and physiology data.

In accordance with an alternative embodiment, a method is provided for mapping physiology information onto an ultrasound-based anatomic structure. The method includes receiving signals from an ultrasound probe located proximate the region of interest and, based upon the receive signals, producing ultrasound data representative of a scan plane including the region of interest. The method further includes generating an ultrasound image based on the ultrasound data. The ultrasound image is representative of an anatomical structure of a portion of the region of interest contained in the scan plane. The method further includes receiving physiology signals from a physiology catheter located proximate the region of interest and, based on the physiology signals, producing physiology data representative of physiologic activity of the portion of the region of interest contained in the scan plane. The method further includes forming a display image by combining the ultrasound image and physiologic data.

DETAILED DESCRIPTION OF THE INVENTION

Figure 1:
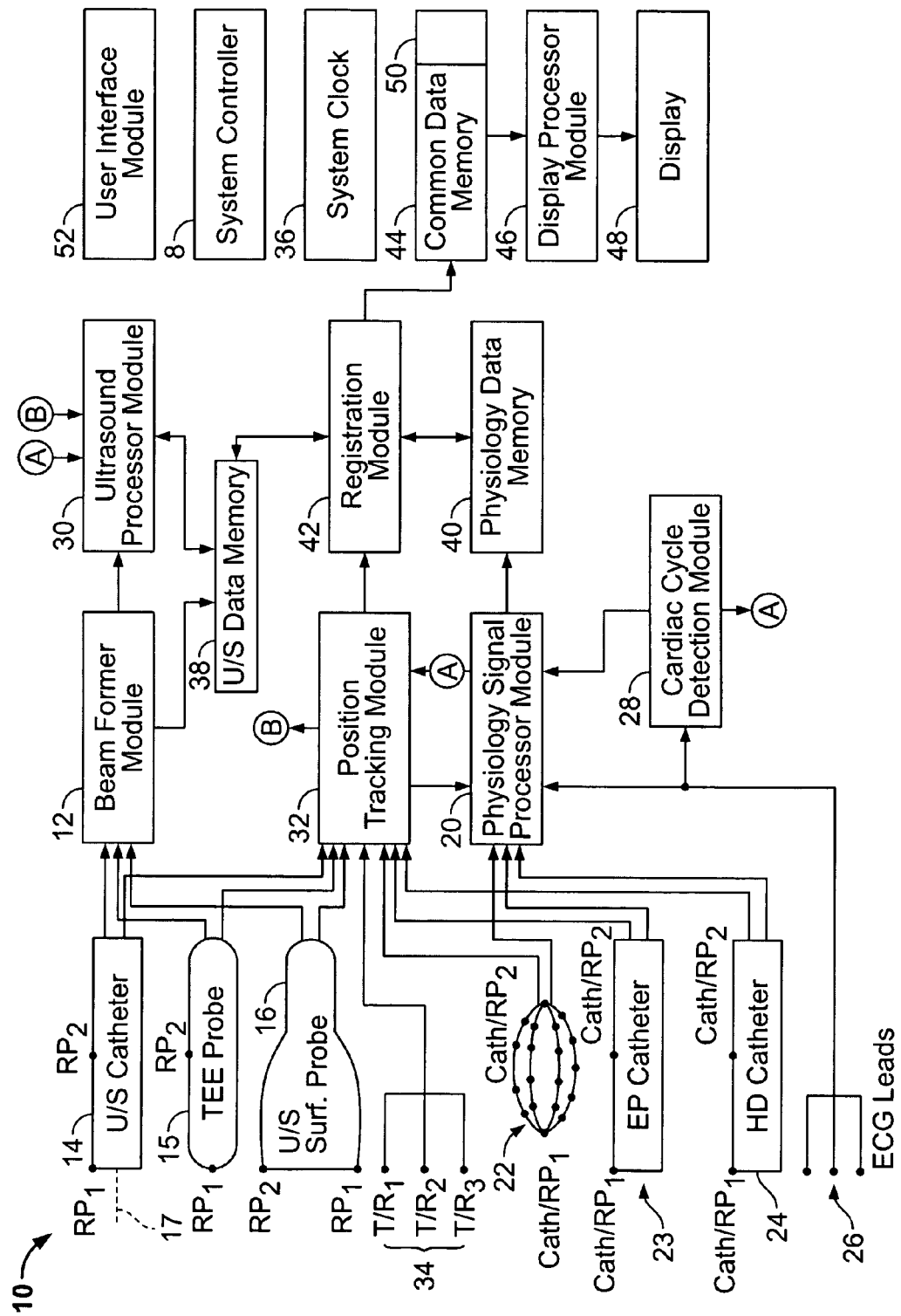
FIG. 1 illustrates a block diagram of a physiology system formed in accordance with an embodiment of the present invention.

FIG. 1 illustrates a physiology system 10 formed in accordance with an embodiment of the present invention. A system controller 8 manages the overall interaction and operation of the various modules, accessories and the like. The physiology system 10 includes a beam former module 12 configured to be joined with one or more ultrasound probes 14-16. Examples of ultrasound probes may include an intravascular ultrasound (IVUS) catheter 14, an echocardiography (ICE) catheter, a transesophageal probe 15, an interventional probe, an ultrasound surface probe 16 and the like. The beam former module 12 controls transmit and receive operations to and from the probes 14-16. A physiology signal processing module 20 is provided and joined with one or more catheters 22-24. Examples of catheters include a basket catheter 22, a multipole electrophysiology catheter 23 (e.g. a 4-pole, 8-pole, 10-pole, 20 pole and the like), a hemodynamic catheter 24 and the like.

The beam former module 12 processes radio frequency (RF) echo signals from one or more of probes 14-16 and produces there from I, Q data pairs associated with each data sample within a scan plane through the region of interest. The beam former module 12 may supply the I, Q data pairs directly to the ultrasound processor module 30. Alternatively or in addition, the beam former module 12 may store the collection of I, Q data pairs defining the sample points within a single scan plane in the ultrasound data memory 38 as raw ultrasound data. The ultrasound data memory 38 stores the I, Q data pairs for individual scan planes as two dimensional data sets, or alternatively for collections of scan planes as three dimensional data sets.

The ultrasound processor module 30 processes the raw I, Q data pairs, as explained below in more detail, to form ultrasound images (2D or 3D). For example, the ultrasound processor module 30 may form B-mode images, color flow images, power Doppler images, spectral Doppler images, M-mode images, ARFI images, strain images, strain rate images and the like. The ultrasound images contain ultrasound image data representing voxels associated with data samples from the region of interest, where the ultrasound image data may be defined in Cartesian or polar coordinates. The ultrasound images may be stored individually as two dimensional data sets. Alternatively, collections of ultrasound images may be stored as three dimensional data sets. The beam former module 12 and ultrasound processor module 30 processes the signals from the ultrasound probe in real-time during a physiology procedure in order that the display 48 is able to display and continuously update the ultrasound image in real-time during the physiology procedure. By way of example, the ultrasound processor module may generate new ultrasound images at a frame rate of at least five frames per second such that the display processor module is able to update the ultrasound image information within the displayed image at a frame rate of at least eight frames per second. Alternatively, the frame rate, at which new ultrasound images are generated and displayed, may be increased to 8, 16, 32 or 64 frames per second or higher.

The physiology signal processor 20 passively and/or actively operates upon one or more of the catheters 22-24 to measure physiology signals. The physiology signal processor module 20 receives physiology signals from one or more of the catheters 22-24 and produces physiology data representative of the physiologic activity of a portion of the regions of interest proximate the sensors on the corresponding catheter 22-24. The physiology data is stored in physiology data memory 40.

ECG leads 26 are provided on the surface of the subject and produce ECG signals that are received by the physiology signal processor module 20 and/or to a cardiac cycle detection module 28. The cardiac cycle detection module 28 monitors the cardiac activity denoted by the ECG signals and generates therefrom timing information representative of cyclical points in the subject's cardiac cycle. The timing information is provided to the physiology signal processor module 20 and to the ultrasound processor module 30.

A position tracking module 32 is joined with a series of detectors 34 that may operate as transmitters and/or receivers. The position tracking module 32, optionally, may also receive position information from one or more of the ultrasound probes 14-16 and/or physiology catheters 22-24. In the example of FIG. 1, the ultrasound probes 14-16 are each provided with first and second reference point elements (denoted RP1 and RP2 on each probe and catheter). The reference point elements may represent transmitters and/or receivers configured to transmit or receive acoustic energy, radio frequency energy, electromagnetic energy and the like. Alternatively, only a single reference point element or sensor may be provided on one or more of the probes and catheters. Examples of conventional sensor configurations and detector systems are described in U.S. Pat. No. 5,713,946 to Ben-Haim; U.S. Pat. No. 6,216,027 to Willis et al.; U.S. Pat. No. 5,662,108 to Budd et al.; U.S. Pat. No. 5,409,000 to Imran; U.S. Pat. No. 6,650,927 to Keidar; U.S. Pat. No. 6,019,725 to Vesely; U.S. Pat. No. 5,445,150 to Dumoulin, all of which are expressly incorporated herein in their entireties by reference.

The position tracking module 32 generates tracking information defining the position of each ultrasound probe and each physiology catheter with respect to a common reference coordinate system. By way of example, the position information may include XYZ coordinates for each reference point element within a common three-dimensional Cartesian coordinate system. Alternatively, the position information may be defined in polar coordinate within a common three-dimensional polar coordinate system. The tracking information may uniquely identify each reference point element, such as through a unique transmit signature and the like. The position tracking module 32 may include a relational table containing an ID for each reference point element uniquely associated with probe/catheter descriptive information (e.g. the serial number, type, dimensions, shape and the like). The tracking information may also include orientation information (e.g. pitch roll and yaw) describing the orientation of a reference axis 17 of a probe or catheter relative to the reference coordinate system.

The position tracking module 32 repeatedly monitors and tracks the reference point element, to generate a continuous stream of coordinate position data sets, wherein a single combination of XYZ values represent a single coordinate position data set. Optionally, the position tracking module 32 may record, with each coordinate position data set, a time stamp indicating a time at which the coordinate position data set was obtained. The time stamp may be defined by a system clock 36 that also provides reference timing information to the physiology signal processor module 20 and ultrasound processor module 30. Alternatively, the time stamp may be defined with respect to the cardiac cycle the patient (e.g. X seconds following/preceding the peak of the R-wave). When the timing information is defined based on the cardiac cycle, cardiac cycle timing information is provided by the cardiac cycle detection module 28 to each of the physiology signal processor module 20, ultrasound processor module 30 and position tracking module 32.

The position tracking module 32 may provide the position information, orientation information and timing information (collectively referred to as "tracking information") to the physiology and ultrasound processor modules 20 and 30. When the tracking information is provided to the ultrasound processor module 30, the ultrasound processor module 30 stores the tracking information with the ultrasound image in the ultrasound data memory 38. The tracking information uniquely identifies the time at which the ultrasound image was acquired, as well as the position and/or orientation of the ultrasound probe 14-16 at the time of acquisition. When the tracking information is provided to the physiology processor module 20, the physiology processor module 20 records the tracking information with the physiology data in the physiology data memory 40. The tracking information uniquely identifies the time at which the physiology data was acquired, as well as the position and/or orientation of the physiology catheter(s) 22-24 at the time of acquisition.

A registration module 42 accesses the ultrasound and physiology data memories 38 and 40 to obtain one or more ultrasound images and related physiology data sets acquired at the same point(s) in time. The ultrasound images and associated physiology data sets are identified from memories 38 and 40 based on the recorded time stamps. The registration module 42 transforms one or both of the ultrasound image and physiology data into a common coordinate system and stores the results in a common data memory 44. By way of example, the registration module 42 may map the physiology data set into the coordinate system defined by the ultrasound images as stored in the ultrasound data memory 38. Alternatively, the registration module 42 may map the ultrasound images into the coordinate system defined by the physiology data sets as stored in the physiology data memory 40. As a further alternative, the registration module 42 may transform both the ultrasound images and physiology data sets into a new coordinate system.

A display processor module 46 accesses the common data memory 44 to obtain select combinations of ultrasound images and physiology data sets for presentation on display 48. The display processor module may form a display image combining the ultrasound image and physiology data set, such that the physiology data is mapped on to an anatomical structure contained in, and defined by, the ultrasound image. Optionally, the display processor module 46 may access a lookup table 50 that is stored as part of, or separate from, the common data memory 44 to define display characteristics, such as transparency, opacity, color, brightness and the like, for individual display pixels defining the resultant display image.

The lookup table 50 may be used to define data samples or voxels within the ultrasound image through one of gray scale and color information, and to define the physiology data through the other of gray scale and color information. Optionally, one combination or range of colors may be designated to denote ultrasound information, while a separate combination or range of colors may be designated to denote physiology data. As a further option, the brightness, intensity or opacity of each pixel in the display image may be varied in accordance with one or both of the value of the ultrasound information and the value of the physiology data. For example, the ultrasound image may be defined by B-mode data values for each data point or voxel, while the physiology data associated with the data point or voxel may be defined by one or more colors within a range of colors (e.g., ranging from blue to red, or ranging from light blue to dark blue, or ranging from light red to dark red). Alternatively, the ultrasound image may be defined by non B-mode data values, such as anatomic M-mode, strain or strain rate characteristics of the anatomic structure, with the strain or strain rate being represented in the display image by discrete colors within a range of colors (e.g., ranging from blue to red, or ranging from light blue to dark blue, or ranging from light red to dark red). When the anatomic structure is represented in the display image by discrete colors, the physiology data may be represented through variations of the brightness at each display pixel.

A user interface 50 to is provided to control the overall operation of the physiology system 10. The user interface 52 may include, among other things, a keyboard, mouse and/or trackball. The user interface 52 may permit an operator to designate a portion of the ultrasound image, for which physiologic data is of interest. The display processor module 46 and/or physiology signal processor module 20 may then generate a separate physiology graph to be displayed independent and distinct from the ultrasound image. For example, the display 48 may present an ultrasound image as a B-mode sector scan, with one or more points of interest on the B-mode sector scan designated. A separate graph may be co-displayed on display 48 with the ultrasound B-mode image.

Figure 2:
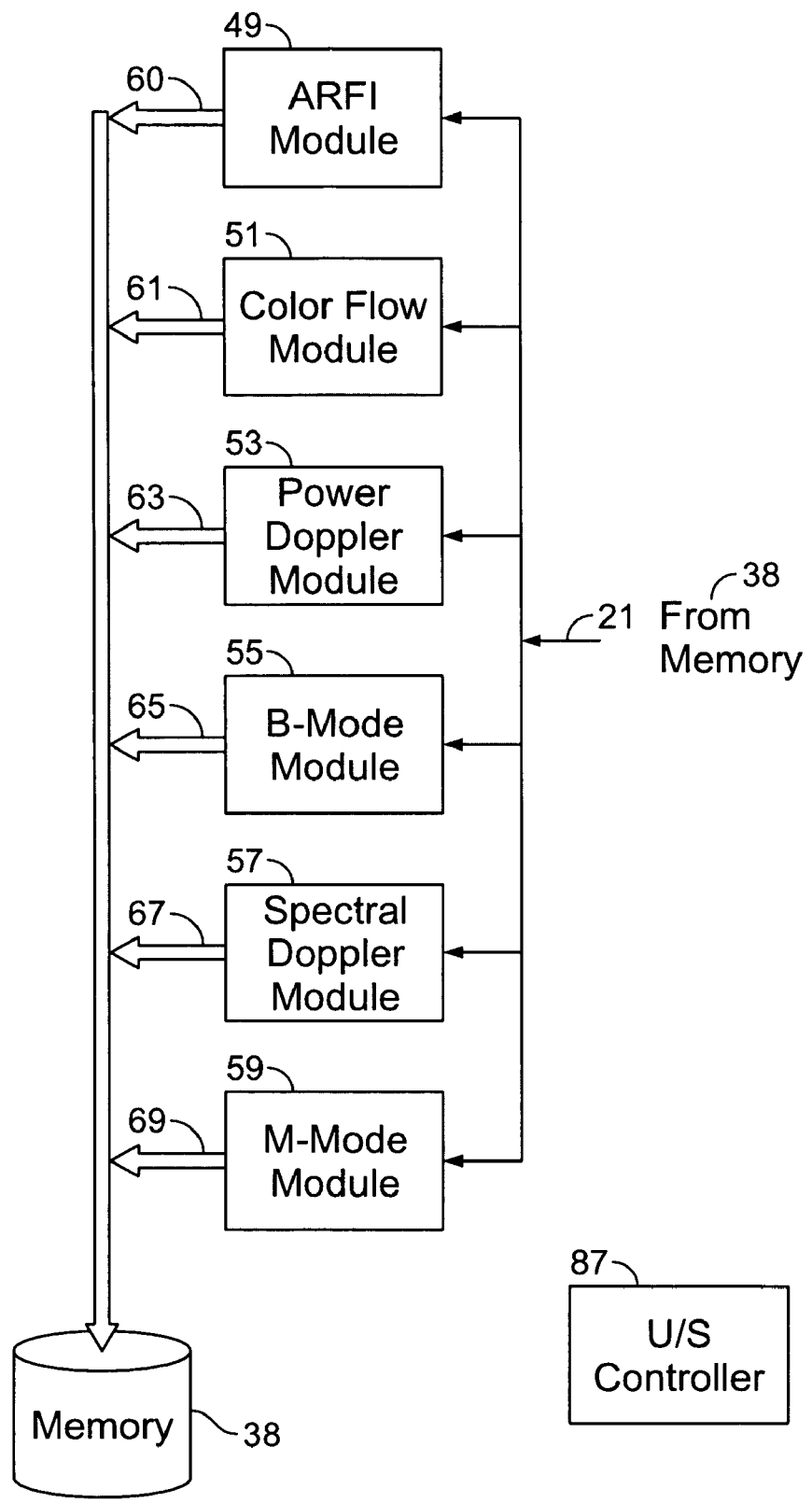
FIG. 2 illustrates a block diagram of the functional modules, within the ultrasound processor module, that are utilized to carry out ultrasound mid-processing operations in accordance with an embodiment of the present invention.

FIG. 2 illustrates an exemplary block diagram of the ultrasound processor module 30 of FIG. 1 formed in accordance with an embodiment of the present invention. The operations of the modules illustrated in FIG. 2 may be controlled by a local ultrasound controller 87 or by the system controller 8. The modules 49-59 perform mid-processor operations.

The ultrasound processor module 30 obtains ultrasound data 21 from the ultrasound data memory 38 or the beam former module 12 (FIG. 1). The received ultrasound data 21 constitutes I, Q data pairs representing the real and imaginary components associated with each data sample. The I, Q data pairs are provided to an ARFI module 49, a color-flow module 51, a power Doppler module 53, a B-mode module 55, a spectral Doppler module 57 and M-mode module 59. Optionally, other modules may be included such as a strain module, a strain rate module and the like. Each of modules 49-59 process the I, Q data pairs in a corresponding manner to generate ARFI data 60, color-flow data 61, power Doppler data 63, B-mode data 65, spectral Doppler data 67, and M-mode data 69, all of which are stored in ultrasound data memory 38. Alternatively, the ultrasound data memory 38 may be divided such that the raw I, Q data pairs are stored in raw data memory, while the processed image data is stored in separate image data memory. The ARFI, color-flow, power Doppler, B-mode, spectral Doppler and M-mode data 60-69 may be stored as sets of vector data values, where each set defines an individual ultrasound image frame. The vector data values are generally organized based on the polar coordinate system.

Figure 3:
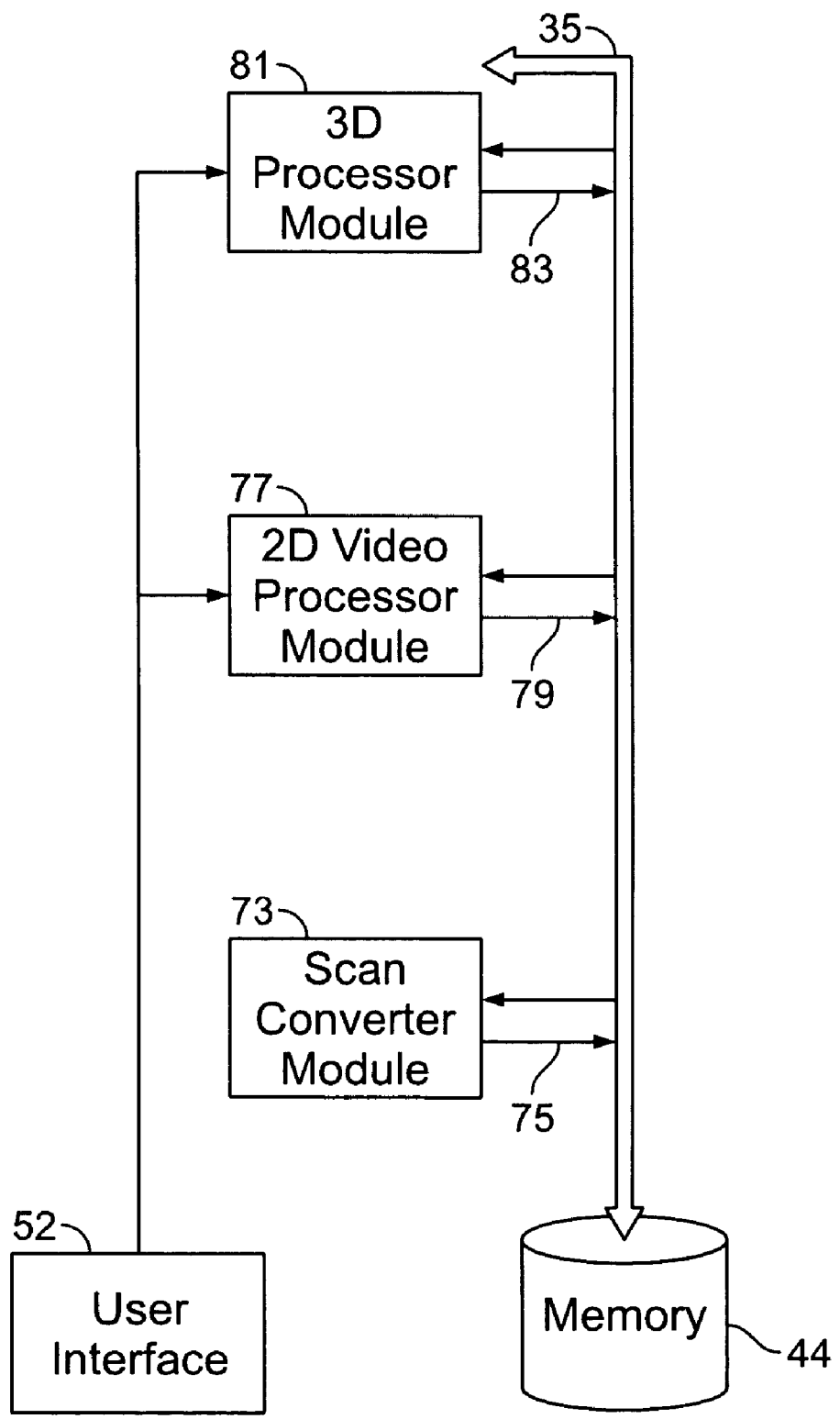
FIG. 3 illustrates a block diagram of the functional modules, within the display processor module, that are utilized to carry out the display processing operations in accordance with an embodiment of the present invention.

FIG. 3 illustrates an exemplary block diagram of the display processor module 46 of FIG. 1 formed in accordance with an embodiment of the present invention. The operations of the modules illustrated in FIG. 3 may be controlled by the local ultrasound controller 87 or by the system controller 8. The modules 73, 77 and 81 perform display-processor operations. A scan converter module 73 reads from memory 44 the vector data values associated with one or more image frames and converts the set of vector data values to Cartesian coordinates to generate a display image frame 75 formatted for display. The ultrasound image frames 75 generated by scan converter module 73 may be passed to a temporary area in memory 44 for subsequent processing or may be passed directly to one of the 2-D and 3-D processor module's 77 and 81. As an example, it may be desired to view a B-mode ultrasound image in real-time associated with the ultrasound signals detected by an ultrasound catheter. To do so, the scan converter obtains B-mode vector data sets for images stored in memory 44. The B-mode vector data is interpolated where necessary and converted into the X,Y format for video display to produce ultrasound image frames. The scan converted ultrasound image frames are passed to the video processor module 77 that maps the video to a grey-scale mapping for video display.

The grey-scale map may represent a transfer function of the raw image data to displayed grey levels. Once the video data is mapped to the grey-scale values, the video processor module 77 controls the display 48 to display the image frame in real-time. The B-mode image displayed in real-time is produced from an image frame of data in which each datum indicates the intensity or brightness of a respective pixel in the display. The display image represents the tissue and/or blood flow in a plane through the region of interest being imaged.

The color-flow module 51 (FIG. 2) may be utilized to provide real-time two-dimensional images of blood velocity in the imaging plane. The frequency of sound waves reflected from the inside of the blood vessels, heart cavities, etc., is shifted in proportion to the velocity of the blood vessels; positively shifted for cells moving toward the transducer and negatively shifted for cells moving away from the transducer. The blood velocity is calculated by measuring the phase shift from firing to firing at a specific range gate. Mean blood velocity from multiple vector positions and multiple range gates along each vector are calculated and a two-dimensional image is made from this information. The color-flow module 51 receives the complex I, Q data pairs from the beamformer module 12 and processes the I, Q data pairs to calculate the mean blood velocity, variance (representing blood turbulence) and total pre-normalized power for all sample volumes within the operator defined region.

The 2D video processor module 77 combines one or more of the frames generated from the different types of ultrasound information and physiologic data. For example, the 2D video processor modules 77 may combine a B-mode image frame and a color representation of the physiologic data by mapping the B-mode data to a grey map and mapping the physiologic data to a color map for video display. In the final displayed image, the color pixel data is superimposed on the grey scale pixel data to form a single multi-mode image frame 79 that may be re-stored in memory 44 or passed over bus 35 to the display 48. Successive frames of B-mode images, in combination with the associated physiology data, may be stored as a cine loop in memory 44. The cine loop represents a first in, first out circular image buffer to capture image data that is displayed in real-time to the user. The user may freeze the cine loop by entering a freeze command at the user interface 52. The user interface 52 represents a keyboard and mouse and all other commands associated with ultrasound system user interface.

The spectral Doppler module 57 (FIG. 2) operates upon the I, Q data pairs by integrating (summing) the data pairs over a specified time interval and then sampling the data pairs. The summing interval and the transmission burst length together define the length of the sample volume which is specified by the user at the user interface 52. The spectral Doppler module 57 may utilize a wall filter to reject any clutter in the signal which may correspond to stationery or very slow moving tissue. The filter output is then fed into a spectrum analyzer, which may implement a Fast Fourier Transform over a moving time window of samples. Each FFT power spectrum is compressed and then output by the spectral Doppler module 57 to memory 44. The 2D video processor module 77 then maps the compressed spectral Doppler data to grey scale values for display on the display 48 as a single spectral line at a particular time point in the Doppler velocity (frequency) versus a time spectrogram. The 2-D video processor module 77 may similarly map the physiology data into a graph representing electrical potential fluctuation (along the vertical axis) and time (along the horizontal axis).

A 3D processor module 81 is also controlled by user interface 52 and accesses memory 44 to obtain spatially consecutive groups of ultrasound image frames and to generate three dimensional image 83 representation thereof, such as through volume rendering or surface rendering algorithms. The three dimensional images 83 may be generated utilizing various imaging techniques, such as ray-casting, maximum intensity pixel projection and the like.

Figure 4:
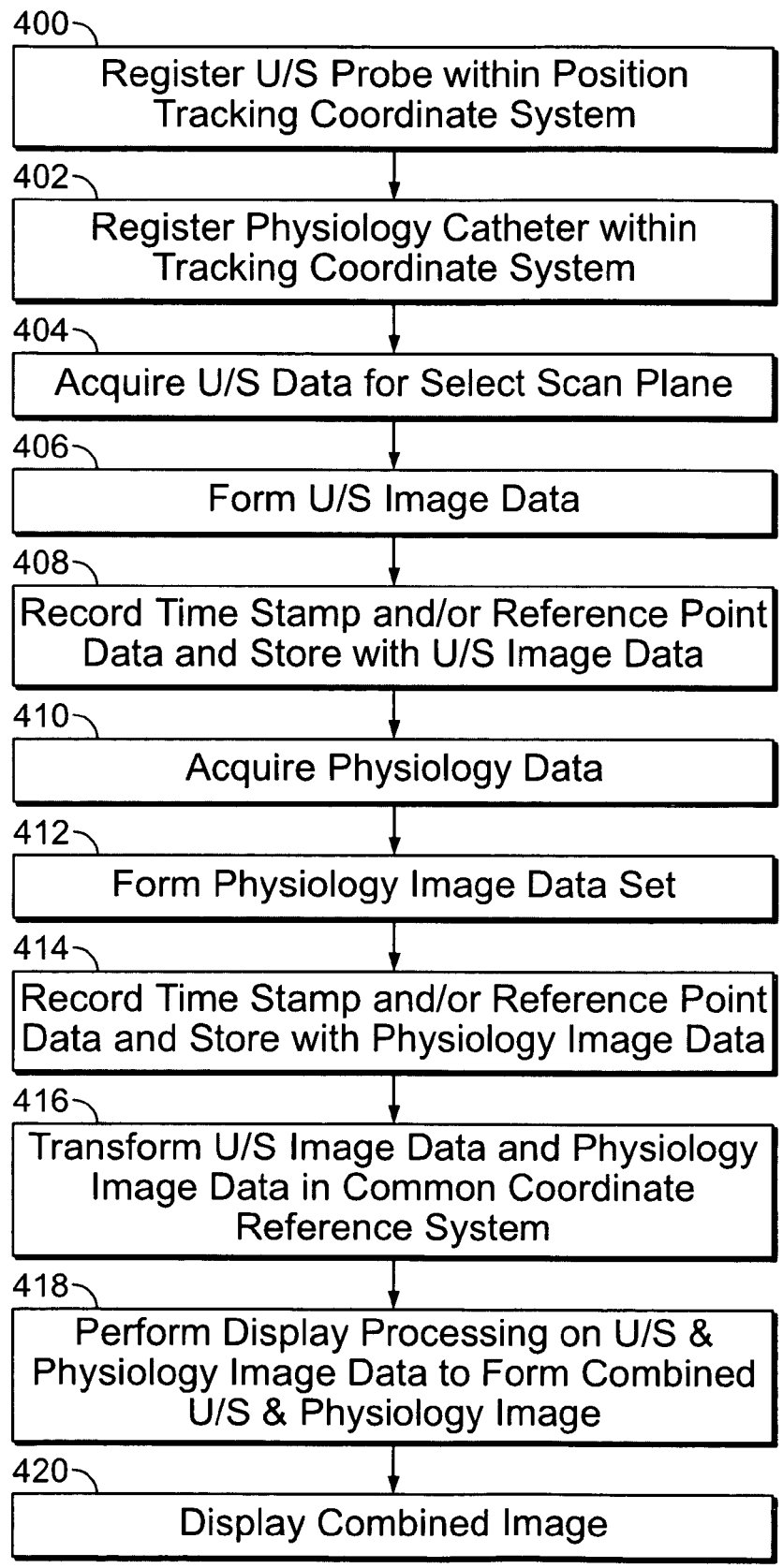
FIG. 4 illustrates a flowchart of the process to acquire, register and display ultrasound images in combination with physiology data.

FIG. 4 illustrates a processing sequence carried out by the physiology system 10 of FIG. 1 in connection with acquiring, tracking and combining ultrasound and physiology data. At 400, the position tracking module 32 registers the ultrasound probe 14-16 within the position tracking coordinate system. At 402, the position tracking module 32 registers the physiology catheters within the position tracking coordinate system. At 404, the beam former module 12 acquires RF echo signals from one or more scan planes of the region of interest and generates I, Q data pairs of therefrom. At 406, the ultrasound processor module 30 accesses the raw I, Q data pairs and forms ultrasound data images therefrom based upon the desired mode of operation (as discussed above in connection with FIG. 2).

At 408, the position tracking module 32 provides tracking information to the ultrasound processor module 30. The tracking information may include a unique time stamp and/or reference point data identifying the position and/or orientation of one or more reference point elements RP1, RP2 on the corresponding ultrasound probe 14-16. The tracking information is stored in memory 38 by the ultrasound processor module 30 with the ultrasound image data.

At 410, the physiology signal processor module 20 acquires physiology data, and at 412, forms a physiology image data set. At 414, the position tracking module 32 provides tracking information (e.g. time stamps and reference point data) to the physiology signal processor module 20. The physiology image data set and tracking information are stored by the physiology signal processor module 20 in physiology data memory 40.

At 416, the registration module 42 accesses the ultrasound and physiology data memories 38 and 40, and transforms or maps the ultrasound and physiology image data into a common coordinate reference system. Once mapped to a common coordinate reference system, the ultrasound and physiology image data are stored in a common data memory 44. At 418, the display processor module 46 performs display processing upon the ultrasound physiology image data to form a combined ultrasound and physiology display image. At 420, the display 48 presents the combined ultrasound and physiology image for viewing.

Figure 5:
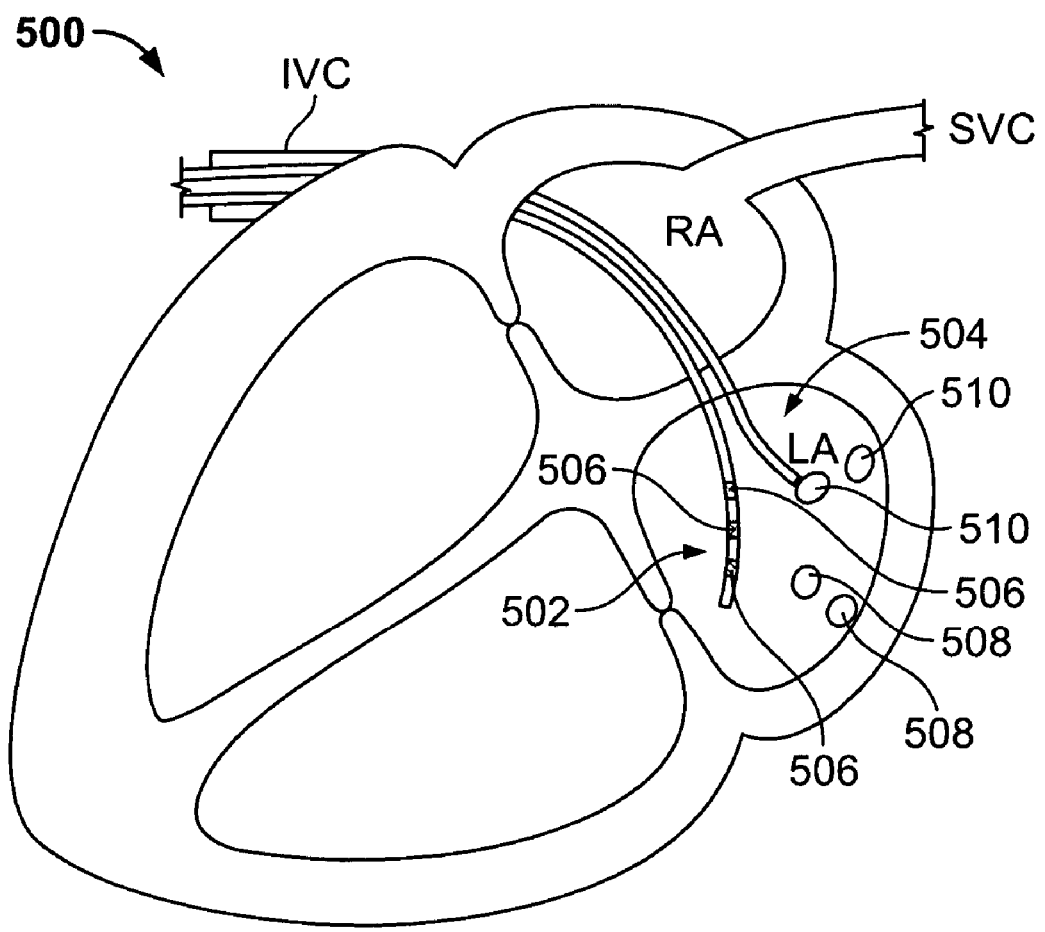
FIG. 5 illustrates an exemplary application by which ultrasound data and physiology data may be acquired in connection with an electrophysiology procedure within the left atrium.

FIG. 5 illustrates an exemplary application in which the above described embodiments may be utilized. The graphical representation of a heart 500 is illustrated. An ultrasound catheter 502 and EP catheter 504 have been inserted through the inferior vena cava (IVC) into the right atrium (RA). The ultrasound and EP catheters 502 and 504 have passed through a punctured opening through the fossa ovalis into the left atrium (LA). The ultrasound catheter 502 includes a series of spaced apart piezo transducers 506 that may be separately activated and controlled to transmit and receive ultrasound data for corresponding scan planes. The ultrasound catheter 502 and EP catheter 504 are utilized to map the anatomical contour of, and electrical activity at, the interior wall of the left atrium, including proximate the openings to the pulmonary veins denoted at 508 and 510. U.S. Pat. No. 5,200,269 describes an exemplary ultrasound catheter that maybe used, the complete object matter of which is incorporated by reference.

ARFI allows examination of the functionality of tissue subsets, such as in the heart, organs, tissue, vasculature and the like. ARFI is a phenomenon associated with the propagation of acoustic waves through a dissipative medium. It is caused by a transfer of momentum from the wave to the medium, arising either from absorption or reflection of the wave. This momentum transfer results in the application of a force in the direction of wave propagation. The magnitude of this force is dependent upon both the tissue properties and the acoustic beam parameters. The duration of the force application is determined by the temporal profile of the acoustic wave. ARFI images the response of tissue to acoustic radiation force for the purpose of characterizing the mechanical properties of the tissue. When the duration of the radiation force is short (less than 1 millisecond), the tissue mechanical impulse response can be observed. ARFI imaging has many potential clinical applications, including: detecting and characterizing a wide variety of soft tissue lesions, and identifying and characterizing atherosclerosis, plaque, and thromboses.

Optionally, imaging may be performed from the right side to the left side of the heart. In this alternative application, the US catheter would remain the HRA and obtain ultrasound images across the septum to the LA where the ablation catheter would be placed.

The term "co-displays" is not limited to displaying information on a common CRT or monitor, but instead refers also to the use of multiple monitors located in immediately adjacent one another to facilitate substantially simultaneous viewing by a single individual. The term "processor" is not intended to be limited to a single processor or CPU.

The various blocks and modules are illustrated as conceptually functional units only, but may be implemented utilizing any combination of dedicated or non-dedicated hardware boards, DSPs, processors and the like. Alternatively, the blocks and modules may be implemented utilizing an off-the-shelf PC with a single processor or multiple processors, with the functional operations distributed between the processors. As a further option, the blocks and modules may be implemented utilizing a hybrid configuration in which certain modular functions are performed utilizing dedicated hardware, while the remaining modular functions are performed utilizing an off-the shelf PC and the like.

It is understood that the operations illustrated in any processing sequences or flowcharts may be carried out in any order, including in parallel.

The figures illustrate diagrams of the functional blocks of various. The functional blocks are not necessarily indicative of the division between hardware circuitry. Thus, for example, one or more of the functional blocks (e.g., processors or memories) may be implemented in a single piece of hardware (e.g., a general purpose signal processor or a block or random access memory, hard disk, or the like). Similarly, the programs may be stand alone programs, may be incorporated as subroutines in an operating system, may be functions in an installed imaging software package, and the like.

What is claimed is:

1. A physiology system, comprising:
    an ultrasound beamformer coupled to receive signals from an ultrasound probe configured to be located proximate a region of interest and, based thereon produce ultrasound data representative of a scan plane including the region of interest;
    an ultrasound (U/S) processor module for generating an ultrasound image, based on the ultrasound data, representative of an anatomical structure of a portion of the region of interest contained in the scan plane;
    a physiology signal processor module coupled to receive physiology signals from a physiology catheter configured to be located proximate the region of interest and, based thereon produce physiology data representative of physiology activity of the portion of the region of interest contained in the scan plane;
    a display processor module forming a display image superimposing an image representation of the physiology data on the ultrasound image; and
    a position tracking module configured to track positions of the ultrasound probe and the physiology catheter, and to generate position information denoting the position of the ultrasound probe and physiology catheter with respect to a common reference coordinate system, the display processor module forming the display image superimposing the image representation of the physiological data on the ultrasound image using the position information.

2. The physiology system of claim 1, wherein the image representation includes color pixel data corresponding to the physiology data, the color pixel data being mapped onto an anatomical structure contained in and defined by the ultrasound image.

3. The physiology system of claim 1, wherein the ultrasound probe constitutes at least one of an intravascular ultrasound (IVUS) catheter, an echocardiography (ICE) catheter, a transesophageal probe, an interventional probe and a surface probe.

4. The physiology system of claim 1, wherein the physiology catheter constitutes at least one of an electrophysiology (EP) catheter and a hemodynamic (HD) catheter.

5. The physiology system of claim 1, further comprising ECG leads provided on the surface of the subject, the ultrasound and physiology signal processor modules including cardiac cycle data, based on signals from the ECG leads, with the ultrasound image and physiology data, respectively.

6. The physiology system of claim 1, wherein the display processor module produces pixel data based on the ultrasound data and the physiology data, the system further comprising an ultrasound/physiology data registration module for registering and transforming the pixel data corresponding to the ultrasound image and the pixel data corresponding to the physiology data into a common coordinate system.

7. The physiology system of claim 1, further comprising a cardiac cycle detection module configured to receive signals from ECG leads placed on a subject, and generate therefrom timing information representative of cyclical points in a subject's cardiac cycle.

8. The physiology system of claim 1, wherein the ultrasound beam former receives signals from the ultrasound probe in real-time during a physiology procedure such that the ultrasound image within the display image is updated in real-time during the physiology procedure.

9. The physiology system of claim 1, wherein the ultrasound processor module generates new ultrasound images, and the display processor module updating the display image, with the new ultrasound images at a frame rate of at least 5 frames per second.

10. The physiology system of claim 1, wherein the ultrasound processor module forms a volumetric ultrasound data set for a series of the scan planes, the display image constituting a three-dimensional representation of the ultrasound image and physiology data.

11. The physiology system of claim 1, wherein the physiology data and ultrasound data combined in the display image are obtained at a common time in a cyclical motion of the region of interest.

12. The physiology system of claim 1, wherein the ultrasound image is representative of least one of B-mode, power Doppler, color flow, M-mode, anatomic M-mode, ARFI mode, strain and strain rate information.

13. The physiology system of claim 1, wherein the image representation of the physiology data is denoted in the display image as at least one of a gray scale image and a color image information combined with the ultrasound image.

14. The physiology system of claim 1, wherein the display processor module accesses a lookup table based on the ultrasound image data and physiology data, the lookup table identifying pixel values to be used in the display image based on the ultrasound image data and physiology data.

15. The physiology system of claim 1, wherein the display processor module presents, in the display image, the ultrasound image data as gray scale information and the image representation of the physiology data as color information.

16. The physiology system of claim 1, further comprising a user interface that permits an operator to designate, in the ultrasound image, a point on the region of interest, the display processor module, in response to the user designation, presenting a graph of physiology data over a period of time associated with a designated point on the region of interest.

17. A method for mapping physiology information onto an ultrasound based anatomic structure, comprising:

receiving signals from an ultrasound probe located proximate a region of interest and, based thereon producing ultrasound data representative of a scan plane including the region of interest;

generating an ultrasound image based on the ultrasound data, the ultrasound image being representative of an anatomical structure of a portion of the region of interest contained in the scan plane;

receiving physiology signals from a physiology catheter located proximate the region of interest and, based thereon producing physiology data representative of physiology activity of the portion of the region of interest contained in the scan plane; and forming a display image superimposing an image representation of the physiology data on the ultrasound image; and tracking position of the ultrasound probe and the physiological catheter and generating tracking information denoting positions of the ultrasound probe and physiology catheter with respect to a common reference coordinate system and forming the display image superimposing the image representation of the physiological data on the ultrasound image using the tracking information.

18. The method of claim 17, wherein the image representation includes color pixel data corresponding to the physiology data, the color pixel data being mapped onto an anatomical structure contained in and defined by the ultrasound image.

19. The method of claim 18, wherein the ultrasound signal is received from an ultrasound probe constituting at least one of an intravascular ultrasound (IVUS) catheter, an echocardiography (ICE) catheter, a transesophageal probe, an interventional probe and a surface probe.

20. The method of claim 17, wherein the physiology data is received from a physiology catheter constituting at least one of an electrophysiology (EP) catheter and a hemodynamic (HD) catheter.

21. The method of claim 17, further comprising receiving ECG signals from ECG leads provided on the surface of the subject; deriving cardiac cycle data, based on the ECG signals, utilizing the cardiac cycle data to synchronize the ultrasound images and physiology data.

22. The method of claim 17, further comprising producing pixel data based on the ultrasound data and the physiology data, and registering and transforming the pixel data corresponding to the ultrasound image and the pixel data corresponding to the physiology data into a common coordinate system.

23. The method of claim 17, further comprising receiving ECG signals from ECG leads placed on a subject, and generating timing information from the ECG signals, the timing information being representative of cyclical points in a subject's cardiac cycle.

24. The method of claim 17, further comprising receiving the ultrasound signals from the ultrasound probe in real-time during a physiology procedure and displaying the ultrasound image updated in real-time during the physiology procedure.

25. The method of claim 17, further comprising generating and displaying new ultrasound images at a frame rate of at least 5 frames per second.

26. The method of claim 17, further comprising forming a volumetric ultrasound data set for a series of the scan planes, the display image constituting a three-dimensional representation of the ultrasound image and physiology data.

27. The method of claim 17, wherein the ultrasound image and physiology data combined in the display image are obtained at a common time in a cyclical motion of the region of interest.

28. The method of claim 17, wherein the ultrasound image is representative of least one of B-mode, power Doppler, color flow, M-mode, anatomic M-mode, ARFI mode, strain and strain rate information.

29. The method of claim 17, wherein the image representation of the physiology data is denoted in the display image as at least one of a gray scale image and a color image combined with the ultrasound image.

30. The method of claim 17, further comprising accessing a lookup table based on the ultrasound image data and physiology data to define pixel values of the display image, the lookup table identifying pixel values to be used in the display image based on the ultrasound image data and physiology data.

31. The method of claim 17, further comprising presenting, in the display image, the ultrasound image data as gray scale information and the image representation of the physiology data as color information.

32. The method of claim 17, further comprising providing a user interface that permits an operator to designate, in the ultrasound image, a point on the region of interest, in response to the user designation, presenting a graph of physiology data over a period of time associated with a designated point on the region of interest.

* * * * *